United States Patent [19]

Feiring

[11] Patent Number: 5,549,603

[45] Date of Patent: *Aug. 27, 1996

[54] METHOD AND APPARATUS FOR INDUCING THE PERMEATION OF MEDICATION INTO INTERNAL TISSUE

[76] Inventor: Andrew J. Feiring, 4454 N. Murray Ave., Milwaukee, Wis. 53211

[ * ] Notice: The term of this patent shall not extend beyond the expiration date of Pat. No. 5,425,703.

[21] Appl. No.: 345,984

[22] Filed: Nov. 28, 1994

Related U.S. Application Data

[63] Continuation of Ser. No. 183,130, Jan. 14, 1994, Pat. No. 8,425,703, which is a continuation of Ser. No. 33,648, Mar. 17, 1993, abandoned, which is a continuation of Ser. No. 520,033, May 7, 1990, Pat. No. 5,236,413.

[51] Int. Cl.$^6$ ............................................. A61B 17/36
[52] U.S. Cl. ............................................. 604/21; 604/96
[58] Field of Search ........................ 604/20–21, 96; 128/783–784, 786–788, 798–802; 607/116

[56] References Cited

U.S. PATENT DOCUMENTS

| | | | |
|---|---|---|---|
| 578,611 | 3/1897 | Rively | 604/21 |
| 600,290 | 3/1898 | Muir | 604/20 |
| 791,730 | 6/1905 | Stanger | 601/20 |
| 866,180 | 9/1907 | Ball | 604/20 |
| 2,123,980 | 7/1938 | Warwick | 604/20 |
| 3,411,507 | 11/1968 | Wingrove | 607/40 |
| 3,618,601 | 11/1971 | Richardson | 604/20 |
| 3,716,054 | 2/1973 | Porter et al. | 604/20 |
| 3,991,755 | 11/1976 | Vernon et al. | 604/20 |
| 4,250,878 | 2/1981 | Jacobson et al. | 604/20 |
| 4,309,989 | 1/1982 | Fahim | 601/2 |
| 4,383,529 | 5/1983 | Webster | 604/20 |
| 4,405,311 | 9/1983 | Greatbatch | 604/20 |
| 4,411,648 | 10/1983 | Davis et al. | 604/21 |
| 4,417,576 | 11/1983 | Baran | 604/101 |
| 4,423,725 | 1/1984 | Baran et al. | 604/101 |
| 4,506,680 | 3/1985 | Stokes | 607/120 |
| 4,569,673 | 2/1986 | Tesi | 604/20 |
| 4,574,807 | 3/1986 | Hewson et al. | 607/27 |
| 4,577,642 | 3/1986 | Stokes | 607/120 |
| 4,752,285 | 6/1988 | Petelenz et al. | 604/20 |
| 4,767,402 | 8/1988 | Kost et al. | 604/22 |
| 4,776,349 | 10/1988 | Nashef et al. | 607/122 |
| 4,915,685 | 4/1990 | Petelenz et al. | 604/20 |
| 4,994,033 | 2/1991 | Shockey et al. | 604/101 |
| 5,135,477 | 8/1992 | Untereker et al. | 604/20 |

FOREIGN PATENT DOCUMENTS

| | | |
|---|---|---|
| 119296 | 9/1984 | European Pat. Off. . |
| 0438078A2 | 7/1991 | European Pat. Off. . |
| 3809815A1 | 10/1989 | Germany . |
| 322202 | 11/1971 | U.S.S.R. . |
| 843999 | 7/1981 | U.S.S.R. . |
| 1069827 | 1/1984 | U.S.S.R. . |
| WO91/19529 | 6/1991 | WIPO . |

*Primary Examiner*—Michael H. Thaler
*Assistant Examiner*—Nancy Mulcare
*Attorney, Agent, or Firm*—Brinks Hofer Gilson & Lione

[57] ABSTRACT

A method and apparatus for selectively treating a targeted portion of internal body tissue of a patient by providing an internal electrode at a point adjacent the tissue to be treated and electrodes external to the patient's body. Fluid containing ionic molecules is supplied to a location between the internal electrode and the external electrodes and an electric field radiating outwardly from the internal electrode to the external electrodes is created so that said fluid flows outwardly away from said internal electrode into the tissue to be treated.

10 Claims, 2 Drawing Sheets

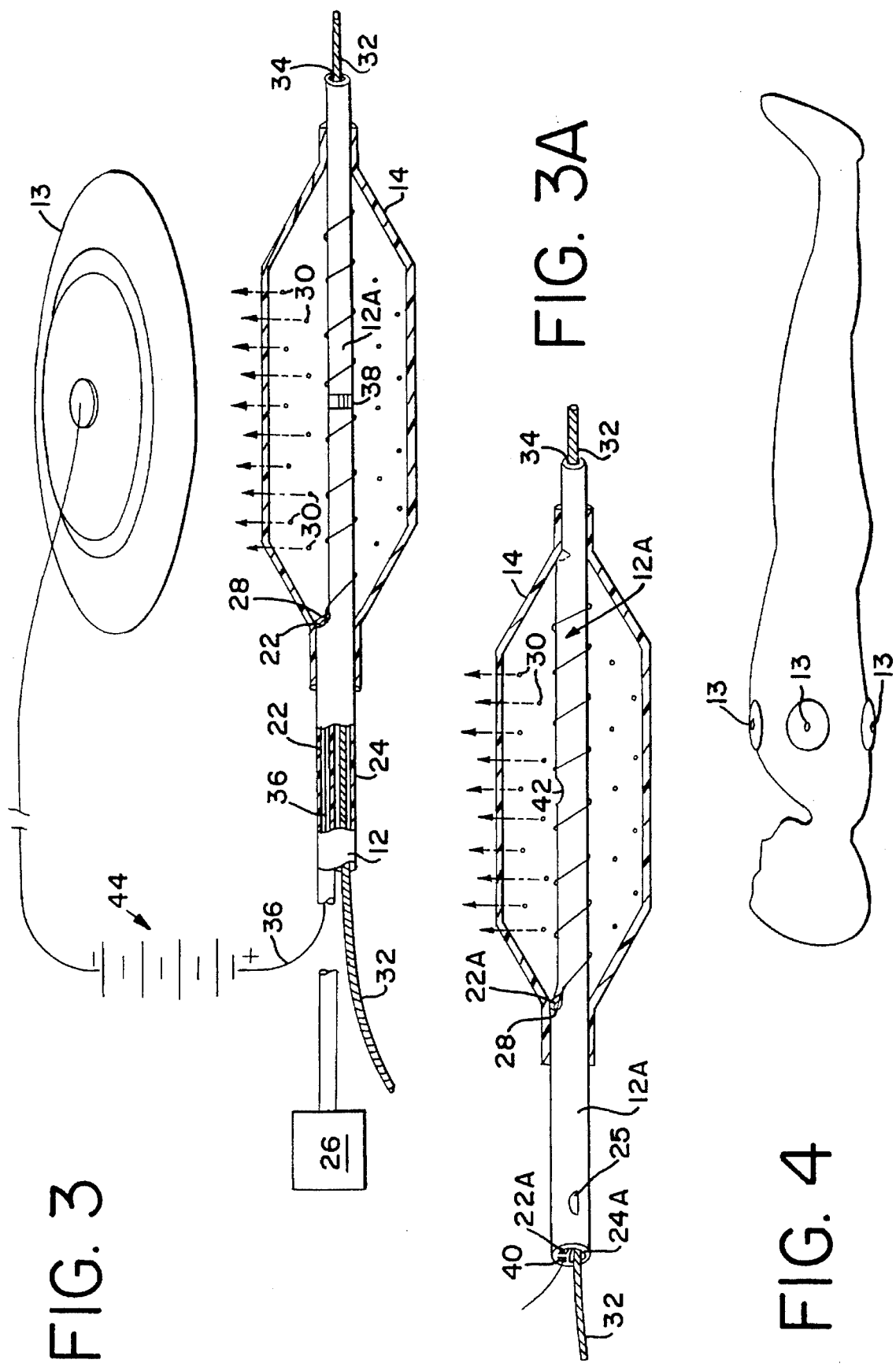

METHOD AND APPARATUS FOR INDUCING THE PERMEATION OF MEDICATION INTO INTERNAL TISSUE

This application is a continuation of application Ser. No. 08/183,130, filed Jan. 14, 1994, now U.S. Pat. No. 5,425,703, which is a Continuation of Ser. No. 08/033,648 filed Mar. 17, 1993, now abandoned, which is a continuation of Ser. No. 07/520,033 filed May 7, 1990, now issued as U.S. Pat. No. 5,236,413.

FIELD OF THE INVENTION

The present invention relates to techniques and devices for inducing the permeation of medication and the like into body tissue and organs.

BACKGROUND OF THE INVENTION

Iontophoresis has been utilized for many years for delivering medication into the body of a patient to diagnose and treat various ailments. Another related procedure iontohydrokinesis has been proposed for similar use. For example, iontophoresis has been utilized to deliver Pilocarpine medication to diagnose cystic fibrosis, for the permeation of insulin through the skin, the introduction of steroids into joints to treat arthritis, to anesthetize the eardrum or eye, to treat plantar warts with sodium salicylate, to treat canker sores in the mouth with steroids, to treat Peyronie's disease (the fibrosing of the penis), and to deliver procainamide across the heart during experimental open chest surgery in dogs.

Iontophoresis involves the transportation of medication in the form of naturally charged or ionic molecules by creating an electric field which acts as a driving force to cause the molecules to advance toward an oppositely charged pole. More particularly, iontophoresis is defined in *Steadman's Medical Dictionary* as the introduction by means of electric current of ions of soluble salts into the tissues of the body for therapeutic purposes; alternatively, the facilitated entry of electrically charged drugs into the surface tissue by application of an electric current. For example, if fluid having charged molecules is placed on a patient's skin and a properly oriented electric field is developed, the fluid will permeate the patient's skin. Where the molecules normally are uncharged, they may be rendered ionic by lowering or raising the pH of the carrying fluid.

The principle is similar for iontohydrokinesis which may be used to deliver uncharged, non-polar molecules of medication. In iontohydrokinesis, water, which has naturally charged molecules and containing noncharged or non-polar molecules of medication, is transported into the tissue of a patient. By subjecting the mixture to an electrical field, the water molecules will carry the uncharged particles with them as they flow from one pole towards the other.

Typically the technique for developing the electric field in iontophoresis or iontohydrokinesis involves placing both positive and negative electrodes externally of the patient's body or the specific organ that is to be treated. Consequently, the techniques do not lend themselves to targeted, localized treatment of internal body organs.

Generally, when it has been desired to use the procedure locally on an internal organ, it has been necessary to expose the organ surgically. Once the organ is exposed, the electrodes can be placed on opposite sides of the organ, as in the case of the delivery of procainamide to the heart during open chest surgery, discussed above. Such a surgical technique for localized treatment of internal organs has obvious drawbacks such as trauma to the patient and other disadvantages and risks of general surgery. It would be desirable, therefore, to provide a less invasive technique for delivering an effective concentration of medication locally to an internal organ. For example, it would be desirable to deliver concentrations of selected compounds to the wall of an artery as an adjunct to angioplasty, a procedure to enlarge a narrowed (stenosed) portion of an artery by placing a balloon in the stenosis and inflating the balloon to dilate the stenosis, thus improving blood flow through the artery.

A significant problem in angioplasty is the relatively high rate of restenosis (approximately 30%) after performing an initial angioplasty. It has been suggested that restenosis may be controlled or possibly prevented by applying suitable medication to the wall of the artery in the region of the angioplasty. For example, among the factors thought to contribute to incidence of restenosis is the uncontrolled proliferation of smooth muscle cells in the arterial wall, as a consequence of the angioplasty. To that end, it has been proposed that a concentrated dose of suitable medication, such as heparin, be applied to a local region of an artery and forced into the wall of the artery under pressure. A catheter adopted for that purpose is disclosed in U.S. Pat. No. 4,636,195 issued Jan. 13, 1987 to Wolinsky. The Wolinsky patent describes a catheter having a pair of spaced balloons mounted on the distal end of the catheter. The catheter is inserted into the patient's arteries and is navigated to the site of the angioplasty. The catheter is positioned so that the balloons embrace the region of the angioplasty. Suitable medication, such as heparin, then is forced, under pressure, into the space between the inflated balloons to force the medication, under pressure, into the wall of the artery.

It is among the objects of the invention, therefore, to provide a minimally evasive technique for delivering an effective concentration of medication or the like locally to an internal organ of the patient.

SUMMARY OF THE INVENTION

In accordance with the invention, medication or the like is cause to permeate through the tissue of a specific, targeted internal body organ using iontophoresis or iontohydrokinesis techniques. Practising the invention involves placing one or more electrodes externally of and circumferentially about the patient. Another electrode is inserted, as by a catheter, into the target organ or a selected portion of the organ. While an electric field is developed between the internal and external electrodes, medication having charged or polar molecules (iontophoresis) or uncharged molecules coupled with polar molecules, such as water (iontohydrokinesis), then may be delivered directly to the internal organ at a location between the internal and external electrodes. The electric field will cause the medication to permeate radially outwardly from the internal electrode toward the external electrodes thus causing the medication to permeate through the target organ.

One embodiment of the invention adapted for use in treating the wall of a blood vessel or other body lumen employs a balloon catheter which may be placed in the blood vessel and positioned by inflating the balloon in the specific portion to be treated. The catheter carries an internal electrode which may be in the form of an insulated wire extending through the catheter and terminating in the exposed electrode inside the balloon. The balloon which also acts as a drug reservoir has a plurality of regularly spaced minute pores. The interior of the inflatable balloon is in communication with a source of liquid medication by a lumen that extends through the catheter from the proximal end where the lumen can be connected to the liquid source. Medication (ionic or coupled to a charged liquid molecule) is delivered to the balloon and weeps through the minute pores during generation of the electric field. When used adjacent the heart, the electric field may be pulsed on during systole to reduce the risk of inducing cardiac arrhythmia.

It is among the objects of the invention to provide a method of inducing permeation of medication to a selected internal organ or body tissue.

Another object of the invention is to provide a method for treating a body organ with a substantial concentration of medicine or drugs, without systematically exposing the patent to such a concentration.

A further object of the invention is to provide a method and apparatus for permeating the wall of an artery with suitable medication so as to reduce the risk of restenosis after angioplasty as well as a primary treatment of obstructive coronary artery disease.

Another object of the invention is to provide a selective medication delivery technique for internal organs using principles of iontophoresis and iontohydrokinesis.

A further object of the invention is to utilize external electrodes and an electrode located in a targeted body organ for creating an electric field to induce the permeation of medication into the targeted body organ by iontophoresis or iontohydrokinesis.

DESCRIPTION OF THE DRAWINGS

The foregoing and other objects and advantages of the invention will be appreciated more fully from the further description thereof, with reference to the accompanying drawings wherein:

FIG. 3 is an enlarged diagrammatic illustration of the catheter in accordance with the invention illustrating the balloon and electrode configuration at the distal end of the catheter;

FIG. 3A is an illustration similar to FIG. 3 illustrating the distal end of the catheter or a three lumen device of the type illustrated in FIG. 2A; and FIG. 4 is a diagrammatic illustration of a patient having multiple electrodes placed circumferentially outside the body.

DESCRIPTION OF THE PREFERRED EMBODIMENTS

Figure 1:
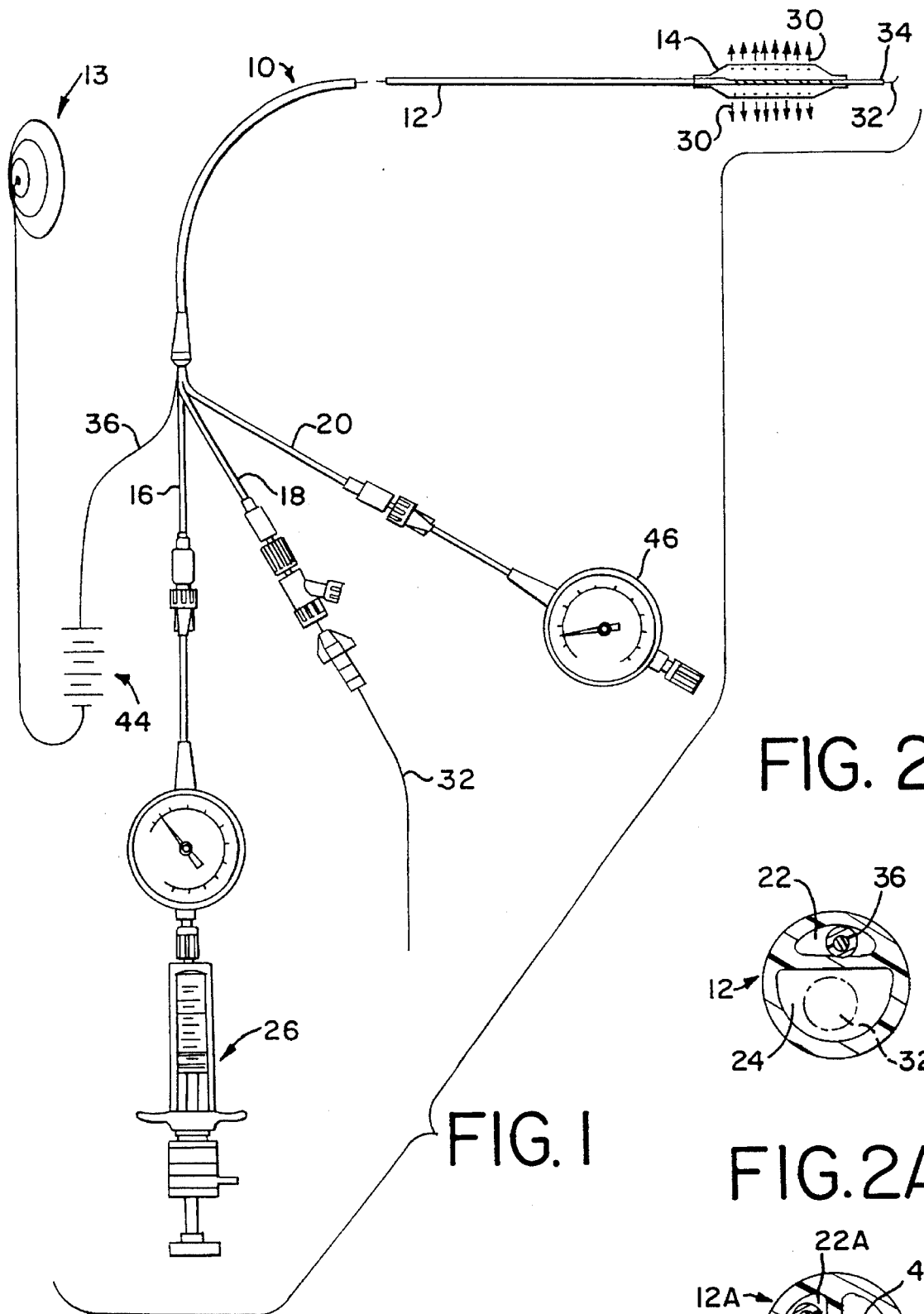
FIG. 1 is a diagrammatic illustration of a system for practising one embodiment of the invention including a balloon catheter having a permeable balloon and a "driving" electrode, and an external "return" electrode.

FIG. 1 illustrates apparatus as it may be used in the practice of the invention. The apparatus includes a catheter 10 and an external return electrode 12. Although only one external electrode 20 is illustrated in FIG. 1, multiple external electrodes preferably are employed and are placed circumferentially about the patient as illustrated in FIG. 4.

As illustrated diagrammatically in FIG. 1, the catheter includes an elongate flexible shaft 12 that may be formed from any of a variety of polymeric materials commonly used in catheter manufacture. The catheter 10 has a proximal end (to the left in FIG. 1) that remains outside of the patient and a distal end (to the right in FIG. 1) that is inserted into the patient. An inflatable and deflatable balloon 14 is mounted to the distal end of the catheter shaft 12. The proximal end of the catheter shaft may branch out into two or three proximal legs including an inflation/deflation leg 16 and a guidewire leg 18 (in the two leg embodiment) and a third fluid return leg 20 (in the three leg embodiment). It should be noted that in the two leg embodiment, return leg 20 is omitted, all three legs 16, 18, 20 being shown in FIG. 1 for convenience of illustration. The catheter may have two or three lumens.

Figure 2:
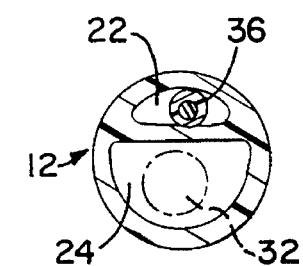
FIG. 2 is a cross-sectional illustration of the catheter shaft in a two lumen embodiment of the invention.

FIG. 2 illustrates, diagrammatically, the cross-sectional configuration of the catheter shaft 12 in a two leg, two lumen embodiment. In this embodiment, the catheter shaft 12 includes an inflation lumen 22 and a guidewire lumen 24. The inflation lumen 22 is in communication with the tubular inflation leg 16 which, in turn, is connected to an inflation/deflation device 26 which may be any of a variety of such devices as are commercially available. The distal end of the inflation lumen 22 opens into the interior of the balloon 14, as indicated diagrammatically at a port 28 in FIG. 3. Thus, the balloon 14 may be inflated and deflated through the lumen 22 by operation of the inflation/deflation device 26. As will be described in further detail, the balloon is formed to include a multiplicity of minute pores 30 which may be substantially regularly spaced about the surface of the balloon 14. The pores 30 serve to deliver the medication to the wall of the organ being treated. The other, larger lumen 24, is connected to the tubular guidewire leg 18 and serves to receive a guidewire 32. The guidewire lumen extends fully the length of the catheter shaft, and terminates at a distal exit orifice 34. The guidewire 32 thus can be projected distally beyond the distal end of the catheter shaft and may be manipulated to facilitate placement of the catheter in the body lumen as will be appreciated by those familiar with the art. For example, the guidewire may be of the steerable type as described in further detail in U.S. Pat. No. 4,545,390 (Leary).

In order to develop the electrical field necessary for iontophoresis or iontohydrokinesis, the catheter includes a conductor that extends from the proximal end of the catheter to and into the balloon 14. In the illustrative embodiment, the conductor is in the form of an insulated wire 36 that may merge into the inflation/deflation lumen 22 at the proximal end of the catheter and may extend distally through the lumen 22 and into the balloon. The distal portion of the conductor 36 disposed within the balloon 14 may be uninsulated to define the inner, driving electrode. Preferably, the driving electrode is wrapped helically about the portion of the shaft 12A that extends through the balloon 14. The helical configuration of the electrode enhances uniform radial distribution of the electrical field. In alternative embodiments, the conductive wire may be conducted to one or more metallic band electrodes extending about the shaft within the balloon, for example, as to a mid-balloon marker band 38. Alternately, the electrode may be in the form of a wire mesh within the balloon about the catheter shaft.

Figure 2A:
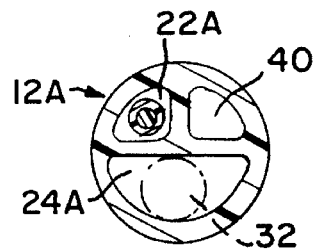
FIG. 2A is a cross-sectional illustration of the shaft of the catheter in a three lumen embodiment of the invention in which the balloon is in communication with two lumens including an inlet lumen and a return lumen.

In the three leg embodiment of the catheter, the catheter includes three lumens as indicated in FIG. 2A. In this embodiment, the catheter shaft 12A is formed to include an inflation lumen 22A, a guidewire lumen 24A and a return lumen 40. The proximal end of the return lumen 40 is connected to the tubular return leg 20 at the proximal end of the catheter. The distal end of the return lumen 40 opens into the interior of the balloon at a port 42 illustrated in FIG. 3A. As will be described further below, the three leg embodiment enables a continuous flow of liquid into and out of the balloon 14.

The size of the balloon 14 is selected so that when inflated it will be slightly larger than the body lumen into which the catheter is to be inserted. This is desirable in order that the balloon may be pressed lightly against the inner luminal surface of the targeted organ so that medication that is emitted from the balloon will be applied directly and intimately against the inner luminal surface of the organ. The minute pores 30 may be of the order of 400 angstroms to 25 microns in diameter. The balloon 14 preferably is made of an inelastic polymeric material of the type used in balloon angioplasty catheters as will be familiar to those skilled in the art. For example, the balloon may be formed from polyethylene terephthalate. The inelasticity of the balloon material serves to prevent the pores 30 from becoming too large during inflation of the balloon, thus undesirably varying the flow rate of the medication.

The external return electrodes 13 and the internal driving electrode are connected to a direct current source 44. In order to reduce the risk of disrupting the patient's heart rhythm when the electrodes are in the region of the heart, the current to the electrodes preferably is pulsed on during the systole phase of the cardiac pumping action and off during diastolic phase.

In use, the external electrodes 20 are positioned circumferentially about the patient. The catheter 10 is inserted into the patient and manipulated into the desired location of the desired body lumen. The catheter 10 may be positioned by any one of numerous well-known methods such as the use of guidewire 32. Once the catheter 10 has been advanced so that the balloon 14 is at the desired location, the balloon 14 is inflated to fill the body lumen and seal the balloon against the inner surface of the body lumen under light pressure. Preferably, the balloon is pressurized not substantially more than approximately 150 mmHg. Power to the electrodes is provided to develop an electric field radiating outward from the inner driving electrode to the outer return electrodes 20. Due to the charged nature of the medication or the water with which the medication may be mixed, the medication flows radially outward along the lines of the electric field, thus permeating the targeted tissue located radially outward from the balloon 14. The medication thus is localized to the target organ.

The external electrodes are positioned, as shown in FIG. 4, about the patient's exterior so that the medication will flow radially outward in all directions. The charge applied to each of the electrodes may be varied when the internal electrode is not located centrally inside the patient so that the field is of equal strength through 360°. The current strength, duration of current application and location of the external electrodes may be varied to further focus the flow of medication. Patch electrodes, which are known in the art, may be used as the external electrodes. Thus, the direction and uniformity of dispersion and permeation of the medication may be controlled. The polarity of the inner driving and external return electrode is selected with reference to the sense of the ionic compound to assure dispersion in a radially outward direction.

The method and apparatus of the present invention provide numerous advantages. By utilizing the electrode configuration of the present invention, specific internal locations of a patient may be targeted for treatment with a particular medication. Furthermore, the permeation of the medication into the body tissue external the balloon is induced by creating an electric field and not by increasing pressure on the liquid in the balloon 14. Consequently, mechanical stress to the body lumen is kept at a minimum. By introducing the medication to the balloon and only allowing it to pass radially outward through the balloon pores, an excessive concentration of medication is not introduced to the patient.

While the foregoing method and apparatus are applicable to a wide variety of body organs and lumens, they have particular use in blood vessels such as arteries. The catheter 10 shown in FIG. 1 may be used in the primary treatment of a lesion (stenosis) with an appropriate medication to reduce the size of the lesion or to prevent restenosis after an angioplasty. In primary treatment of a lesion, the catheter 10 is inserted into an artery until the balloon 14 is positioned against the region of the dilated stenosis. A suitable liquid medication (ionic or coupled to a polar carrier molecule) is infused into the balloon 14 to inflate the balloon and seal it against the luminal surface. An electric field then is induced between the internal driving electrode and the external return electrodes 13 so that the medication flows radially outward through the pores 30 of the balloon 14 and into the arterial wall to break down the stenotic material and cause reduction in the size of the stenosis.

When used for treating an artery after a conventional angioplasty to prevent restenosis, an antirestenosis drug, such as heparin, is used to inflate the balloon 14. Once the electric field has been induced, the heparin or other appropriate medication will flow outwardly and permeate the arterial wall. The degree to which the medication permeates the wall can be controlled by varying the strength of the electric field and the length of time that the electric field is maintained. In the illustrated catheter, the inflation of the balloon 14 shuts off blood flow through the artery during the procedure. The present method may be employed in an autoperfusion catheter of the type described in U.S. Pat. No. 4,581,017 (Sahota) to allow blood flow through the catheter to distally perfuse the artery while the balloon is inflated. As described in that patent, the disclosure of which is hereby incorporated by reference in its entirety, an opening is provided in the catheter shaft wall proximally of the balloon to allow blood to perfuse through the catheter distally of the balloon.

It sometimes may occur that the ionic charge of the molecule may change during the procedure, for example, if the pH of the fluid changes. Such pH change may result from interaction of the liquid with the electrode as may be a function of the duration of the procedure. In order to avoid adverse changes in pH, the liquid may be aspirated periodically from the catheter and replaced with fresh liquid. This procedure may be used with the two lumen configuration described above and illustrated in FIGS. 1 and 2. Alternately with the three lumen embodiment, represented by FIG. 2A, a continuous flow of liquid may be established through the balloon, flow of liquid being toward and into the balloon through the inflation lumen 22A and out of and away from the balloon through the return lumen 40. The return leg 20 at the proximal end of the catheter 10 preferably is provided with a variable flow resistor 46 by which the back pressure of the returning outflowing liquid may be controlled. By operating the inflation device and variable restrictor 46, the pressure developed within the balloon and rate of continuous flow through the system may be controlled as desired.

Thus, I have described the invention by which medication may be applied selectively to a targeted internal organ or body lumen, such as an artery. It should be understood, while the invention has been described with regard to treatment of tissue adjacent a body lumen, the invention may be practiced in any location where it is desired to apply medication to a vessel or organ having a lumen accessible by a catheter. For example, the apparatus may be utilized to treat the heart or coronary arteries. The catheter may be passed into a lumen in a particular organ or may even be inserted into a lumen formed in an organ or tumor for the express purpose of receiving the catheter.

It should be understood that the foregoing description of the invention is intended merely to be illustrative thereof and that other embodiments, modifications and equivalents may be apparent to those skilled in the art without departing from its spirit.

Having thus described the invention, what I desire to claim in the letters patent is:

1. An apparatus for selectively inducing the permeation of liquid to a targeted portion of internal tissue in the body of a patient comprising:

at least one external electrode positioned outside of the patient's body, said external electrode means adapted to extend circumferentially about a portion of the patient's body;

a catheter having an elongate shaft, the catheter having proximal and distal ends;

means extending along the shaft for delivering said liquid from the proximal end to the distal region of the catheter;

means for emitting said liquid from the catheter;

an internal electrode carried by the catheter at the distal end of the catheter;

conductor means extending through the catheter shaft and being electrically connected to the internal electrode, the proximal end of the conductor being connectible to a source of electrical energy; and means for inducing an electric field between said internal electrode and said at least one external electrode so that fluid emitted from the distal end of the catheter will flow in a direction extending from the internally placed electrode outwardly toward the external electrode.

2. An apparatus as defined in claim 2 wherein the balloon is formed from a substantially inelastic material.

3. An apparatus as defined in claim 4 wherein the catheter further comprises a lumen extending through the catheter shaft and terminating in an outlet distally beyond the balloon, and means for directing blood flow through the lumen and out of the distal outlet to permit distal perfusion during inflation of the balloon.

4. A catheter for selectively inducing the permeation of liquid to a targeted portion of internal tissue in the body of a patient comprising:

an elongate shaft having proximal and distal ends;

means extending along the shaft for delivering said liquid from the proximal end of the catheter to the distal region of the catheter;

a flexible, inflatable balloon mounted to the distal end of the catheter shaft, the balloon formed from a substantially inelastic material, the balloon having a plurality of pores formed therethrough to enable the liquid to flow out of the pores;

an internal electrode carried by the catheter at the distal end of the catheter;

conductor means extending through the catheter shaft and being electrically connected to the internal electrode, the proximal end of the conductor being connectible to a source of electrical energy.

5. An apparatus as defined in claim 4 wherein the catheter further comprises a lumen extending through the catheter shaft and terminating in an outlet distally beyond the balloon, the lumen being adapted to receive blood proximally of the balloon and to enable blood to flow through the catheter and be emitted distally of the balloon to permit distal perfusion during inflation of the balloon.

6. An apparatus for selectively inducing the permeation of liquid to a targeted portion of a blood vessel in the body of a patient comprising:

at least one external electrode adapted to be positioned outside of the patient's body;

a catheter having an elongated flexible shaft dimensioned for insertion into the human vascular system, the catheter having proximal and distal ends, means extending along the shaft for delivering said liquid from the proximal to the distal region of the catheter and for emitting said liquid from the catheter;

an internal electrode carried by the catheter at the distal end of the catheter;

a plurality of external electrodes adapted to be positioned circumferentially about a portion of the patient's body;

conductor means extending through the catheter shaft and being electrically connected to the internal electrode, the proximal end of the conductor being connectible to a source of electrical energy; and means for inducing an electric field between said internal electrode and said at least one external electrode so that fluid emitted from the distal end of the catheter will flow in a direction extending from the internally placed electrode outwardly toward the external electrode.

7. An apparatus as defined in claim 6 wherein the means for emitting said fluid comprises a flexible, inflatable balloon mounted to the distal end of the catheter shaft, the balloon formed from a substantially inelastic material which prevents growth of the pore size as the balloon is inflated, the balloon having a plurality of pores formed therethrough to enable the liquid to flow out of the pores.

8. An apparatus as defined in claim 7 wherein the catheter further comprises a lumen extending through the catheter shaft and terminating in an outlet distally beyond the balloon and means for directing blood flow through the lumen and out of the distal outlet to permit distal perfusion of blood during inflation of the balloon.

9. A catheter for selectively inducing the permeation of liquid to a targeted portion of a blood vessel in the body of a patient comprising:

an elongated flexible shaft dimensioned for insertion into the human vascular system, said shaft having proximal and distal ends;

means extending along the shaft for delivering said liquid from the proximal end of the catheter to the distal region of the catheter;

a flexible, inflatable balloon mounted to the distal end of the catheter shaft the balloon is formed from a substantially inelastic material and has a plurality of pores formed therethrough to enable the liquid to flow out of the pores;

an internal electrode carried by the catheter at the distal end of the catheter; and conductor means extending through the catheter shaft and being electrically connected to the internal electrode, the proximal end of the conductor being connectible to a source of electrical energy.

10. An apparatus as defined in claim 9 wherein the catheter further comprises a lumen extending through the catheter shaft and terminating in an outlet distally beyond the balloon, the lumen being adapted to receive blood proximally of the balloon and to enable blood to flow through the catheter and be emitted distally of the balloon to permit distal perfusion during inflation of the balloon.

* * * * *

UNITED STATES PATENT AND TRADEMARK OFFICE
CERTIFICATE OF CORRECTION

PATENT NO. : 5,549,603
DATED : August 27, 1996
INVENTOR(S) : Andrew J. Feiring

Page 1 of 2

It is certified that error appears in the above-indentified patent and that said Letters Patent is hereby corrected as shown below:

In the Title

In each occurrence of the title, delete "METHOD AND".

On the Title Page

In column 1, under "Related U.S. Application Data" line 2, delete "8,425,703" and substitute --5,425,703--.

Under "References Cited U.S. PATENT DOCUMENTS", in column 2, please insert the following:

```
--873,021    12/1907   Cool ..................604/21
 4,877,831   10/1989   Conway et al. ........606/194
 4,892,519    1/1990   Songer et al. ........606/194
 4,944,745    7/1990   Sogard et al. ........606/194
 5,232,441    8/1993   Stephen et al. .......604/21
 5,047,028    9/1991   Qian .................604/49
 5,236,413    9/1993   Feiring ..............604/21
 5,282,785    2/1994   Shapland et al. ......604/21
 5,286,254    2/1994   Shapland et al. ......604/21
 5,304,120    4/1994   Crandell et al. ......604/21
 4,581,107    4/1986   Sahota ...............604/101
```

UNITED STATES PATENT AND TRADEMARK OFFICE
CERTIFICATE OF CORRECTION

PATENT NO. : 5,549,603
DATED : August 27, 1996
INVENTOR(S) : Andrew J. Feiring

It is certified that error appears in the above-indentified patent and that said Letters Patent is hereby corrected as shown below:

In claim 2, line 1, delete "2" and substitute --1--.

In claim 3, line 1, delete "4" and substitute --2--.

In claim 9, line 11, after "shaft", insert ",".

Signed and Sealed this

Eighteenth Day of November 1997

BRUCE LEHMAN

*Attest:*

*Attesting Officer*        *Commissioner of Patents and Trademarks*